United States Patent
Patton

(10) Patent No.: US 7,873,404 B1
(45) Date of Patent: Jan. 18, 2011

(54) METHOD FOR PERFORMING ANGIOPLASTY AND ANGIOGRAPHY WITH A SINGLE CATHETER

(75) Inventor: Chris Patton, Manhattan Beach, CA (US)

(73) Assignee: Seth Caplan, Studio City, CA (US), part interest ( * ) Notice: Subject to any disclaimer, the term of this patent is extended or adjusted under 35 U.S.C. 154(b) by 0 days.

(21) Appl. No.: 12/475,438

(22) Filed: May 29, 2009

Related U.S. Application Data

(60) Provisional application No. 61/057,177, filed on May 29, 2008.

(51) Int. Cl.
*A61M 25/00* (2006.01)

(52) U.S. Cl. .......... 600/433; 600/434; 604/28; 604/264; 606/191; 606/192

(58) Field of Classification Search .......... 600/424, 600/431, 433, 434, 435; 604/28, 93.01, 96.01, 604/102.02, 102.03, 99.01–99.04, 101.01–101.05, 604/508–510
See application file for complete search history.

(56) References Cited

U.S. PATENT DOCUMENTS

| | | | |
|---|---|---|---|
| 4,445,892 A | 5/1984 | Hussein et al. | |
| 4,944,745 A | 7/1990 | Sogard | |
| 4,994,033 A | 2/1991 | Shockey | |
| 5,085,635 A * | 2/1992 | Cragg | 604/102.03 |
| 5,090,959 A * | 2/1992 | Samson et al. | 600/116 |
| 5,135,484 A * | 8/1992 | Wright | 604/28 |
| 5,180,366 A | 1/1993 | Woods | |
| 5,282,785 A | 2/1994 | Shapland | |
| 5,286,254 A | 2/1994 | Shapland | |
| 5,295,962 A | 3/1994 | Crocker | |
| 5,312,344 A * | 5/1994 | Grinfeld et al. | 604/101.05 |
| 5,389,314 A | 2/1995 | Wang | |
| 5,425,703 A | 6/1995 | Feiring | |
| 5,439,446 A | 8/1995 | Barry | |
| 5,460,610 A * | 10/1995 | Don Michael | 604/101.03 |
| 5,462,529 A | 10/1995 | Simpson | |
| 5,554,119 A | 9/1996 | Harrison | |
| 5,591,129 A | 1/1997 | Shoup | |
| 6,149,641 A | 11/2000 | Ungs | |
| 6,159,195 A | 12/2000 | Ha | |
| 6,231,588 B1 | 5/2001 | Zadno | |
| 6,338,709 B1 | 1/2002 | Geoffrion | |
| 6,488,672 B1 * | 12/2002 | Dance et al. | 604/509 |
| 6,623,452 B2 | 9/2003 | Chien | |
| 7,025,762 B2 | 4/2006 | Johnston | |
| 7,108,684 B2 | 9/2006 | Farnan | |
| 7,163,533 B2 | 1/2007 | Hobbs | |
| 7,313,431 B2 | 12/2007 | Uber | |
| 2001/0044648 A1 * | 11/2001 | Wolinsky et al. | 623/1.15 |
| 2002/0115649 A1 * | 8/2002 | Woodburn et al. | 514/185 |
| 2003/0100924 A1 * | 5/2003 | Foreman et al. | 607/9 |
| 2004/0133232 A1 * | 7/2004 | Rosenbluth et al. | 606/200 |
| 2008/0255447 A1 * | 10/2008 | Bourang et al. | 600/434 |

* cited by examiner

*Primary Examiner*—Brian Casler
*Assistant Examiner*—James Kish
(74) *Attorney, Agent, or Firm*—Thomas M. Freiburger

(57) ABSTRACT

A combination catheter enables performing an angiogram and an angioplasty (and repetitions of one or both) with the same catheter instrument, without removal from and re-insertion into an artery until the procedure is completed.

3 Claims, 3 Drawing Sheets

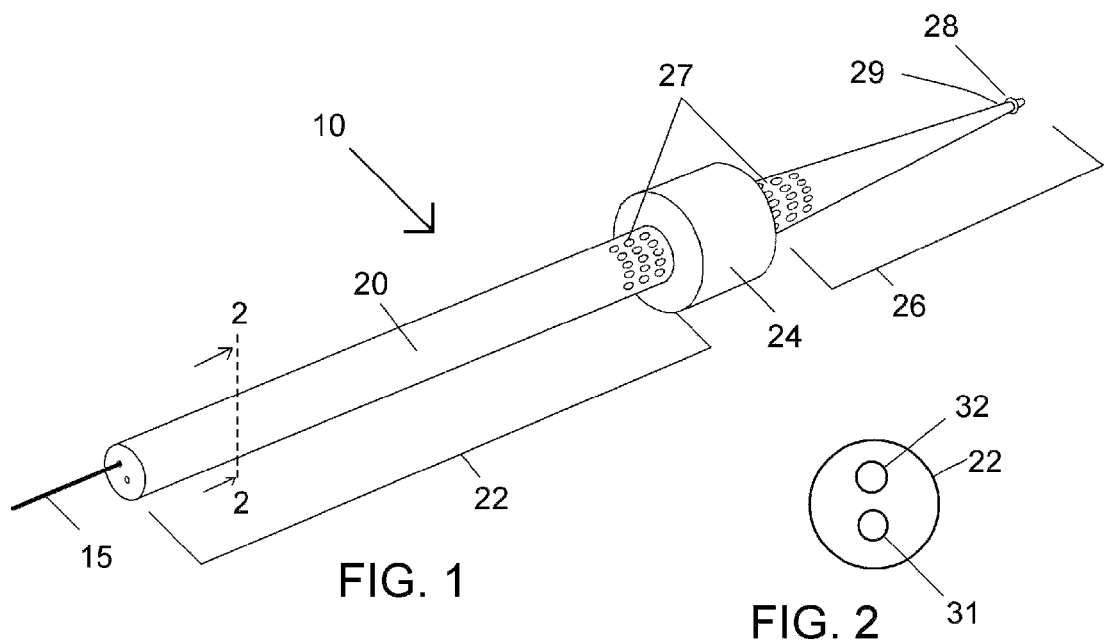
FIG. 1
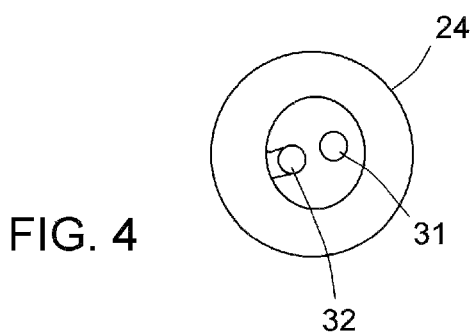
FIG. 2
FIG. 4

METHOD FOR PERFORMING ANGIOPLASTY AND ANGIOGRAPHY WITH A SINGLE CATHETER

BACKGROUND OF THE INVENTION

This application claims benefit of provisional application Ser. No. 61/057,177 filed May 29, 2008.

The present invention relates generally to intravascular balloon catheters used to conduct venograms, angiograms and angioplasties, and more particularly, to a device that facilitates such procedures using a single catheter.

The blockage of arterial blood vessels, i.e. atherosclerosis, is a common disorder that can have serious consequences. The narrowing or blockage of arteries can result in potentially fatal conditions such as coronary heart disease and myocardial infarctions. Other damaging narrowing or blockages can occur in non-coronary arteries and veins throughout the body. The blockages resulting from such disorders can lead to further complications where permanent injury or death is possible.

A number of medical procedures have been developed to aid in the detection, reduction, and elimination of such blockages. An angiogram is one technique for detecting the extent of a blockage. A common type of angiogram allows the visualization of the blood in the arteries. To perform the angiogram, a diagnostic catheter is used to administer the X-ray contrast agent in the area to be visualized. Distribution of the contrast agent within the arteries allows X-ray visualization of the size of the artery openings.

Once a narrowing or blockage has been identified using an angiogram, a separate procedure is then used for treatment. A balloon angioplasty is a common method for treating a narrowing or blockage by mechanically widening the blood vessel. A balloon angioplasty must be performed using a separate catheter from the diagnostic catheter used to perform the initial angiogram.

A similar procedure known as a venogram can be used to diagnose and treat disorders of the veins. The present invention, as will be described below, can be used in connection with both angiograms and venograms. For the purposes of clarity in the following description it will be understood by those of skill in the art that references to angiograms or angioplasty will apply with equal effectiveness to venograms.

Multiple angiograms and angioplasties may be needed when the narrowing or blockage is extensive. As a result, an extensive procedure would require the use of multiple catheters to separately perform the angiogram and the angioplasty. Furthermore, having to exchange the diagnostic catheter and the balloon catheter to perform each procedure can increase the duration of the overall procedure. Exchanging between a diagnostic catheter and a balloon catheter during a procedure may also lead to various health complications.

Bleeding is one risk associated with catheterization. There is a general risk of bleeding anytime the skin is pierced. The risk of severe bleeding increases at the site where the catheters are inserted. Accordingly, removal and insertion of catheters may result in greater blood loss.

Infections are another risk associated with catheterization. The removal and insertion of multiple catheters into a lesion increases the risk of exposing harmful bacteria and agents into the bloodstream.

Arteries and veins generally travel along with nerves. There is a risk of injuring nerves when a catheter is inserted across a lesion. Such nerve injury may lead to numbness. Although such injury is not necessarily fatal, it can lead to much discomfort. Inserting and re-inserting separate catheters may increase the risk of damaging a nerve.

Injury to blood vessels is a more serious risk associated with catheterization. Complications, such as torn blood vessels, can unnecessarily risk the health of the patient and may require surgery, which increases the costs and risks to the patient. Moreover, patents may also experience increased swelling or bruising at points where the catheters were inserted. Removing and re-inserting individual catheters for angiograms and angioplasties can increase these risks.

Inserting catheters across the same lesion becomes increasingly difficult with each subsequent attempt. Accordingly, exchanging catheters increases the risk of losing access across the lesion. This further contributes to unnecessary delay and increased risks to the patient.

Therefore, it is the object of the present invention to combine the attributes of a diagnostic angiogram catheter with a balloon angioplasty catheter, so that a single catheter can facilitate both procedures. In doing so, the present invention helps reduce or eliminate the complications associated with having to use separate catheters to perform angiograms and angioplasties.

The use of a single catheter also results in a significant time savings for the completion of the surgical process. This is beneficial for a number of reasons. Shortening the time that the patent is undergoing surgery reduces the chance of infection or other complications, and promotes healing. A surgeon is able to treat more patients in a given time period. This increases efficiencies and reduces the cost of patient care.

SUMMARY OF THE INVENTION

A device useful for angioplasty and angiograms is described. In one embodiment, the device comprises a catheter and a guide wire. The catheter consists of a hollow central channel and a balloon. The guide wire is adapted to fit within the hollow central channel of the catheter, referred to as a lumen, a second lumen within the catheter connects to the balloon for inflation. The catheter incorporates a series of openings adjacent to the balloon. Contrast can be expelled through the series of openings to perform an angiogram. The contrast agent typically is an iodine dye that permits the surgeon to examine the internal structure of the artery. The contrast agent shows up clearly when examined using x-ray imaging techniques such as fluoroscopy. This can give a detailed image of the internal structure of an artery or veins.

After performing the angiogram with the device of the invention, the surgeon can inflate the balloon of the device to perform an angioplasty if necessary.

In an example procedure using the device, the guide wire is first advanced into the blood vessel. Then, the catheter is advanced over the guide wire until the series of openings corresponds with the site of the prospective angioplasty. Contrast is then injected into the catheter and expelled through the openings. An angiogram is performed utilizing the ejected contrast. The results of the angiogram can be used to confirm the desired location of an angioplasty. Next, the catheter is retracted until the balloon portion is at the desired position in the blood vessel. The balloon is then inflated, performing an angioplasty. Finally, a second angiogram can be performed to confirm the success of the angioplasty. Notably, only one catheter is needed to perform both the angioplasty and the angiogram(s).

In another embodiment, the device again comprises a catheter and a guide wire. The catheter is composed of multiple lumens and a balloon. On either side of the balloon the catheter contains several openings adjacent to the balloon. This embodiment also includes a valve tip located at the distal end of the catheter, the tip being self-closing when the guide wire is pulled back. This embodiment is similarly capable of being used for concurrent angiograms and angioplasties. In addition, the multiple lumens allow for the introduction of multiple dyes or contrasts into the blood vessel.

A feature of the invention is that the catheter can be left in the patient after the above procedure so that therapeutic medications can be introduced into the bloodstream using thrombolytic therapy.

DESCRIPTION OF THE DRAWINGS

FIG. 1 is a perspective view showing a distal end portion of the combination catheter angioplasty device of the present invention.

FIG. 2 is a cross-sectional view of the device of the invention taken along the line 2-2 in FIG. 1.

FIGS. 4, 5 and 6 are sectional views taken at the balloon or just proximal to the balloon in different embodiments.

DESCRIPTION OF PREFERRED EMBODIMENTS

In the following description, for the purposes of explanation, specific devices, method steps and arrangements are set forth in order to provide a more thorough understanding of the invention. It will be apparent to those skilled in the art, however, that the invention may be practiced without these specifically enumerated details and that the preferred embodiment can be modified so as to provide other capabilities. In some instances, well-known structures and methods have not been described in detail.

FIG. 1 shows in perspective the angioplasty device of the invention. The angioplasty device 10 comprises a combination catheter 20 and a guide wire 15. What is shown is only the distal end of the catheter illustrating the features of the invention. Like conventional vascular catheters, the catheter is very long. In medicine, a catheter typically refers to a tube that can be inserted into a body cavity or duct. Catheters used in angioplasty are adapted to be inserted into major arteries that make up portions of the body's vascular system. Catheters are typically manufactured from a variety of different polymers, including silicone rubber latex and thermoplastic elastomers. Silicone is one of the most common choices because it is inert and non-reactive to body fluids and a range of medical fluids with which it might come into contact. In the present invention, the combination catheter 20 is flexible, and able to bend into a variety of different configurations and shapes. This type of catheter is known in the art as a "soft" catheter.

Figure 3:
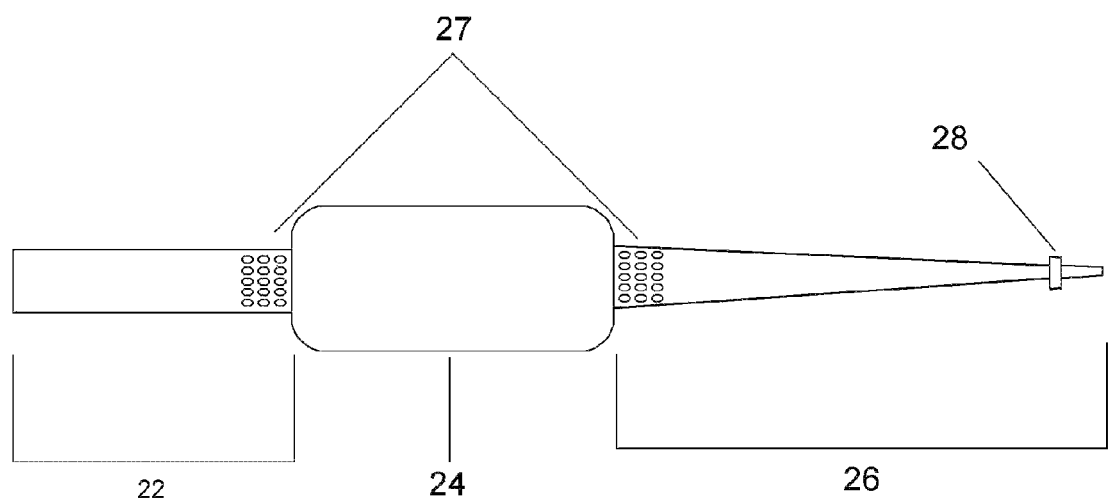
FIG. 3 is a side view showing an inflatable angioplasty balloon and contrast-dispensing holes utilized in the device.

Referring now to all of FIGS. 1, 2 and 3, the device 20 includes a first catheter portion 22, which is attached at one end to an inflatable angioplasty balloon 24, shown schematically. The angioplasty balloon 24 in turn is attached to a second catheter portion 26, the catheter structure continuing through the balloon. Exit holes 27 are provided in the catheter, preferably (but not necessarily) both distal and proximal of the balloon. At a minimum at least one exit hole is provided; preferably the holes are positioned such that they extend around the periphery of the catheter. Located at the distal end of the combination catheter 20 is a valve tip 28 and the second catheter portion 26 preferably tapers to a narrow distal end 29 at the valve tip 28.

The catheter has the shape of a long, flexible tube. The angioplasty device is intended to be inserted into a patient's artery. The combination catheter 20 is therefore sized accordingly. In the preferred embodiment, the first and second catheter portions 22 and 26 have a diameter that corresponds to standard sizes used in the industry. These standard sizes are referred to in French sizes (3 Fr=1 mm), and one typical size is about 5 French (3 and 4 Fr are also used). The first catheter portion 22 can vary in length, and has a much greater length than schematically depicted. In a preferred embodiment, the catheter ranges in size from about 40 cm to 120 cm. The particular length that is chosen will depend on the specific therapeutic purpose for which the catheter will be used on a patient; dimensions given herein are not limiting, but are intended to show the typical size of the catheter device that will be commonly used.

The cross section of the combination catheter 20 is illustrated in FIG. 2, as seen along the plane 2-2 in FIG. 1. As shown, in a preferred embodiment there are two channels or lumens 31 and 32 that run along the long axis of the combination catheter 20. The first lumen 31 is used to accept the guide wire 15 (not shown in FIG. 2), and extends along the entire length of the combination catheter 20. It terminates at the distal end of the catheter at the valve tip, which is described in more detail below. The first lumen 31 provides a pathway for the guide wire which has first been inserted in the patient's artery and which supports and guides the catheter device as it is advanced into the artery. The first lumen 31 preferably is connected to the openings 27 in the side of the catheter (unless more than two lumens are provided).

Referring again to FIG. 1, during an angiogram, a contrast agent is inserted into the first lumen 31 and exits through the openings or series of exit holes 27, the lumen 31 preferably being larger in diameter than the guide wire to allow the contrast liquid to be delivered without removing the guide wire. The second lumen 32 is used to inflate the angioplasty balloon 24 during an angioplasty procedure. The second lumen 32 does not extend the length of the entire catheter. Rather, it ends at and is connected directly to the angioplasty balloon 24. FIG. 4 is another cross section taken inside the balloon, showing the lumens 31 and 32. This section is essentially at the distal end of the lumen 32, showing the lumen fluidly connected to the balloon interior.

Figure 5:
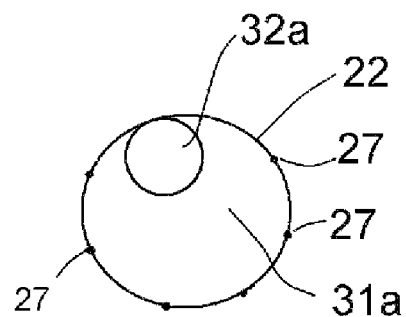
Figure 6:
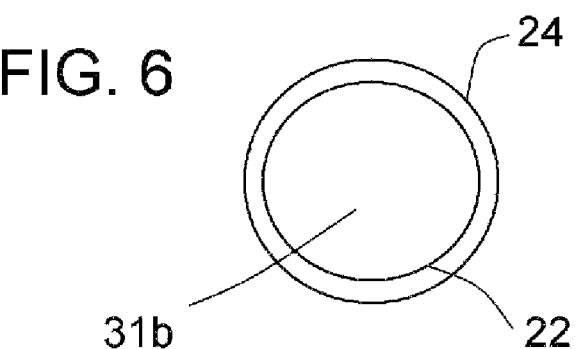

FIGS. 5 and 6 show another embodiment of the two lumens, these being cross section views just proximal to the balloon (FIG. 5) and at the balloon (FIG. 6). FIG. 5 shows that the balloon inflation channel or lumen can comprise a smaller tube 32a positioned within the basic catheter tube 22. The guide lumen 31a is thus defined by the main space within the larger tube 22. At the balloon, the tube 32a has a terminal, closed end, and a side hole (not shown) in the small tube and through the wall of the catheter body 22 is in fluid communication with the interior of the balloon, similar to what is shown in FIG. 4. FIG. 6 shows the balloon 24 surrounding the basic catheter tube 22, just distal of the distal end of the inflation lumen or channel 32a, with the space 31b within the tube 22 comprising the guide lumen. In FIG. 5 the holes for administering contrast agent are shown schematically at 27.

In an alternative embodiment of the invention, additional lumens (not shown) can be added to the combination catheter 20. The additional lumens can, for example, facilitate the delivery of medication or additional contrast as needed by the patient.

The guide wire 15 is substantially circular in cross-section (although other cross-sections can be used with equal effectiveness). It is sized so that it will fit in one of the lumens illustrated in FIGS. 2, 4, 5 and 6 and discussed above. In a preferred embodiment the guide wire has a diameter in the approximate range of 0.018 to 0.035 inches (about 1.4 French to about 2.7 French). As is well known, the guide wire is sufficiently rigid so that it can be inserted (pushed) into the patient's arteries or veins. At the same time, the guide wire has enough flexibility to permit it to conform to curves or deviations present in the arteries. The guide wire preferably is not of the same rigidity along its entire length; the distal end is substantially more flexible. This prevents the guide wire from inadvertently puncturing the walls of the veins or arteries as it is being inserted.

As noted above, the first and second catheter portions 22 and 26 preferably both include series of exit holes 27 that are located adjacent to the inflatable angioplasty balloon 24. These holes are disposed around the entire circumference of the combination catheter 20. They provide openings from the first lumen or channel 31 (or 31a) to the exterior of the combination catheter 20, for administering the contrast agent. Although two sets of holes 27 are shown, one proximal and one distal of the balloon 24, the device 10 can be provided with only series of holes, at one of these locations. The catheter is capable of being shifted on the guide to adjust its proximal/distal position in the blood vessel so that one set of holes can be sufficient for delivering the contrast agent at the location desired.

The valve tip 28 comprises a flexible rubber or plastic material that is located at the distal end of the catheter device 10. The valve tip 28 surrounds the end of the lumen 31, which may comprise the interior volume of the second catheter portion 26. When the guide wire 15 is fully inserted in the catheter device it passes through an opening in the distal end 29, pushing and holding the valve tip 28 open. When the guide wire is withdrawn, the valve tip occludes the opening. The resilient nature of the valve tip, which may be connected to the catheter distal end 29 by integral plastic or rubber material, causes it to close and substantially seal against the distal end 29 in the event the guide wire is pulled back. In an alternative embodiment, the catheter is without the valve tip 28; instead, the distal end 29 narrows significantly to a small diameter such that the guide wire 15 substantially fills and occludes the distal end 29 and thus closes the lumen 31. In a third embodiment the catheter tip tapers to such a small opening (which can be pushed larger by the guide wire when present) that the tip opening strongly impedes contrast flow, so that contrast is expelled out the exit holes 27, even without the guide wire present. In any of these embodiments the opening at the distal end 29 is substantially sealed when contrast medium is administered, preventing any substantial amount of contrast from flowing through the distal end. This arrangement causes the contrast agent to exit through the exit holes 27 thereby facilitating the angiogram.

The foregoing description has made reference to the first catheter portion 22, inflatable angioplasty balloon 24 and second catheter portion 26. These various elements are not necessarily separate components, and in a preferred embodiment, at least the catheter portions 22 and 26 will be produced as a single unit during the manufacturing process. The balloon can also be included with the original extruded catheter, in a known blow molding process. The reference to the various elements herein is only intended to provide a clear illustration of the structure and operation of the invention. It will also be apparent to those of skill in the art that in alternative embodiments the first catheter portion 22, inflatable angioplasty balloon 24 and second catheter portion 26 could all be manufactured separately and joined together in a final assembly process, along with the inner balloon-inflation lumen 32 and any other inner lumen other than the catheter body interior.

Figure 7:
FIG. 7 is a schematic side view showing a modified form of the combination catheter device.

An alternative configuration for the angioplasty catheter device 10a is shown in FIG. 7. Here, the distal end 29a of the catheter device is formed in a bend as shown, to provide steerability of the catheter through relatively tight turns in the artery. Angled-tip catheters are known for devices different from those of the invention.

In operation of the angioplasty device of the invention, a physician first identifies an area of interest inside a patient's artery or vein that requires treatment. The area of interest can be identified using common treatment techniques well known in the art. The physician then commences treatment by inserting the guide wire 15 into the patient's artery, in the normal manner. The combination catheter 20 is placed over the guide wire and advanced until the inflatable angioplasty balloon 24 has passed the area of interest (or lesion) which requires treatment, or until one set of exit holes 27 is properly adjacent to the area of interest for delivery of contrast. The guide wire 15 is then either left in place, for the embodiment in which the guide wire lumen 31 is oversized and the guide wire is relied on to close the distal catheter end 29, or the guide wire is pulled back or removed from the artery by withdrawing it from the combination catheter 20. In the latter case the valve tip 28 seals off the lumen, preventing blood from entering the device and contrast liquid from flooding out the end.

The physician then injects liquid contrast agent through the lumen 31 in the combination catheter. This can be through the lumen 31 with the guide wire in place, or with the guide wire removed. The liquid passes through the holes 29 and into the artery. An angiogram can then be performed, using methods well known to those of skill in the art. It will be assumed for the purposes of illustration that the results of the angiogram indicate that angioplasty is required to treat the patient. (If angioplasty is not required, the catheter can be withdrawn, and the treatment process is concluded.)

The combination catheter 20 is pulled back slightly (or moved forward along the guide wire, depending on catheter position, position of holes and presence or absence of guide wire) until the angioplasty balloon 24 is adjacent to the lesion. The angioplasty balloon 24 is inflated by using a pressurized liquid injected through the second lumen 32 of the catheter. After an appropriate period of time, the angioplasty balloon is deflated. The combination catheter 20 is again moved so that the angioplasty balloon 24 is no longer over the lesion, but with holes 27 in position to deliver contrast medium appropriately. The physician then performs a post-angioplasty angiogram using the methods described above. If the results of the angiogram indicate that additional angioplasty is required, then the catheter can be moved, and the angioplasty balloon 24 re-inflated. Again, the guide wire can be left in place during these steps, in one embodiment of the invention. After the physician is satisfied that the angioplasty has had its desired effect, the catheter is withdrawn from the patient's artery.

It will be apparent to those skilled in the art that the foregoing description is for illustrative purposes only, and that various changes and modifications can be made to the present invention without departing from the spirit and scope of the invention. The full extent of the present invention is defined and limited only by the following claims.

I claim:

1. A method of conducting angiography and angioplasty, comprising the steps of:

(a) inserting a guide wire into a patient's blood vessel;

(b) placing a combination catheter over the guide wire, the combination catheter including at least two lumens, at least one inflatable angioplasty balloon, and at least one exit hole formed into a side wall of the catheter adjacent to the inflatable angioplasty balloon,
(c) delivering contrast liquid into one lumen of the combination catheter and through the at least one exit hole and into the blood vessel, and performing angiography with the contrast liquid in the blood vessel,
(d) diagnosing the resulting angiogram to determine blockage of the blood vessel to thus identify a lesion,
(e) positioning the combination catheter such that the angioplasty balloon is located adjacent to the lesion in the patient's blood vessel,
(f) inflating the angioplasty balloon against the blood vessel so as to perform angioplasty,
(g) deflating said angioplasty balloon,
(h) positioning the combination catheter so that the exit hole is in position to deliver contrast liquid appropriately for angiography,
(i) repeating steps (c) and (d), and
(j) when continued blockage is indicated by angiography in step (i), repeating steps (e) through (j), and when continued blockage is not indicated, withdrawing the combination catheter and the guide wire from the patient's blood vessel.

2. The method of claim 1, wherein, prior to step (c), the guide wire is removed, the removal of the guide wire being effective to cause a distal end of a lumen through which the guide wire was positioned to close.

3. The method of claim 1, wherein said one lumen in which the contrast liquid is delivered is a first lumen and also receives the guide wire, and wherein said first lumen leads to an end opening at the distal end of the combination catheter, the distal end opening being sized to fit closely over the guide wire, and wherein the contrast liquid is delivered through said first lumen with the guide wire present, the first lumen being larger than the guide wire to allow the flow of contrast liquid, and the guide wire inhibiting flow of contrast liquid out said distal end opening of the combination catheter.

* * * * *